US011912788B2

(12) United States Patent
Cella et al.

(10) Patent No.: US 11,912,788 B2
(45) Date of Patent: *Feb. 27, 2024

(54) PROBIOTIC MOLECULES FOR REDUCING PATHOGEN VIRULENCE

(71) Applicant: MICROSINTESIS INC., Oakville (CA)

(72) Inventors: Monica Angela Cella, Stratford (CA); Sarah M. Curtis, Atikokan (CA); Jonathon Patrick Roepke, Charlottetown (CA)

(73) Assignee: MICROSINTESIS INC., Oakville (CA)

(*) Notice: Subject to any disclaimer, the term of this patent is extended or adjusted under 35 U.S.C. 154(b) by 0 days.

This patent is subject to a terminal disclaimer.

(21) Appl. No.: 16/494,429

(22) PCT Filed: Mar. 16, 2018

(86) PCT No.: PCT/CA2018/050320

§ 371 (c)(1),
(2) Date: Sep. 16, 2019

(87) PCT Pub. No.: WO2018/165765

PCT Pub. Date: Sep. 20, 2018

(65) Prior Publication Data

US 2020/0017547 A1 Jan. 16, 2020

Related U.S. Application Data

(60) Provisional application No. 62/472,061, filed on Mar. 16, 2017.

(51) Int. Cl.

| | |
|---|---|
| ***C07K 7/06*** | (2006.01) |
| ***A23L 33/18*** | (2016.01) |
| ***A23L 33/195*** | (2016.01) |
| ***A61L 15/46*** | (2006.01) |
| ***A61L 27/54*** | (2006.01) |
| ***A61L 29/16*** | (2006.01) |
| ***A61L 31/16*** | (2006.01) |
| ***C07K 5/107*** | (2006.01) |
| ***C07K 5/113*** | (2006.01) |
| ***A61K 38/00*** | (2006.01) |

(52) U.S. Cl.

CPC ................ *C07K 7/06* (2013.01); *A23L 33/18* (2016.08); *A23L 33/195* (2016.08); *A61L 15/46* (2013.01); *A61L 27/54* (2013.01); *A61L 29/16* (2013.01); *A61L 31/16* (2013.01); *C07K 5/1016* (2013.01); *C07K 5/1021* (2013.01); *A61K 38/00* (2013.01); *A61L 2300/25* (2013.01); *A61L 2300/404* (2013.01)

(58) Field of Classification Search

CPC ................................ A61K 39/00; A61K 39/02
USPC ...... 424/9.1, 9.2, 184.1, 185.1, 190.1, 234.1
See application file for complete search history.

(56) References Cited

U.S. PATENT DOCUMENTS

| | | | | |
|---|---|---|---|---|
| 5,846,732 | A | 12/1998 | Collin et al. | |
| 2004/0031072 | A1 | 2/2004 | La Rosa et al. | |
| 2007/0027308 | A1 | 2/2007 | Milne Edwards et al. | |
| 2009/0075904 | A1 | 3/2009 | Boots | |
| 2009/0214498 | A1 | 8/2009 | Ross et al. | |
| 2011/0105385 | A1 | 5/2011 | Lu et al. | |
| 2011/0262400 | A1* | 10/2011 | Griffiths .................... | A61P 1/14 424/93.4 |
| 2013/0330335 | A1 | 12/2013 | Bremel et al. | |
| 2015/0044188 | A1 | 2/2015 | Griffiths | |
| 2015/0218229 | A1 | 8/2015 | Hrincius et al. | |
| 2020/0017547 | A1 | 1/2020 | Cella et al. | |

FOREIGN PATENT DOCUMENTS

| | | | | |
|---|---|---|---|---|
| EP | 0395309 | A1 | 10/1990 | |
| JP | 2016536310 | A | 11/2016 | |
| WO | 9418832 | A1 | 9/1994 | |
| WO | 2004092206 | A1 | 10/2004 | |
| WO | WO-2005074837 | A1 * | 8/2005 | ......... B05B 13/0207 |
| WO | 2009/155711 | | 12/2009 | |
| WO | 2011135513 | A1 | 11/2011 | |
| WO | 2014020209 | A1 | 2/2014 | |
| WO | 2014035345 | A1 | 3/2014 | |
| WO | 2015021530 | A1 | 2/2015 | |
| WO | 2015063608 | A2 | 5/2015 | |
| WO | 2016172722 | A1 | 10/2016 | |
| WO | 2018165764 | A1 | 9/2018 | |

OTHER PUBLICATIONS

Written Opinion of International Search Report corresponding to International Patent Application No. PCT/CA2019/050320, dated Jun. 7, 2018, 10 pages.
Extended European Search Report corresponding to European Application No. 18766973.4, dated Nov. 20, 2020 10 pages.
Extended European Search Report corresponding to European Patent Application No. 18768492.3, dated Dec. 17, 2020 9 pages.
Written Opinion and International Search Report corresponding to International Patent Application No. PCT/CA2018/050319, dated Jun. 4, 2018, 16 pages.
Liu, Yufang , et al., "Identification and quantification of bioactive peptides in milk and kefir", Retrieved from the Internet: URL:https://d-nb.info/1136473270/34 2017.
Lu R. et al. "Isolation, identification and characterization of small bioactive peptides from Lactobacillus GG conditional media that exert both anti-Gramnegative and Gram-positive bactericidal activity" J Pediatr Gastroenterol Nutr, 49(1):23-30 2009.

(Continued)

*Primary Examiner* — Brian Gangle
(74) *Attorney, Agent, or Firm* — Myers Bigel, P.A.

(57) ABSTRACT

Provided are peptides that are derived from probiotic bacteria that have use for preventing and/or treating non-enteric infections in a subject. The peptides derived from the probiotic bacteria also have use for reducing the virulence of non-enteric infections in a subject. Also provided are compositions of the peptides formulated as or within food products, beverages, nutritional supplements, medicaments and the like.

7 Claims, 2 Drawing Sheets

Specification includes a Sequence Listing.

(56) References Cited

OTHER PUBLICATIONS

Fazeli et al., "Lactobacillus acidophilus and its Inhibitory Effect on Pyelonephritis Associated Pili and Outer Membrane Protein Expression in *Escherichia coli*", Journal of Pure & Applied Microbiology, 2014;8(Spl. Edn. 2):549-555.

Written Opinion issued in corresponding Singapore Application No. 11201909602T, dated Jul. 5, 2022 (including English translation).

Jinsmaa, et al., "Enzymatic release of neocasomorphin and β-casomorphin from bovine β-casein", Peptides, 20(8), 1999, 957-962.

Kohmura, et al., "Inhibition of Angiotensin-converting Enzyme by Synthetic Peptides of Human β-Casein", Agricultural and Biological Chemistry, 53(8), 1989, 2107-2114.

Sarheed, et al., "Chapter 17—Antimicrobial Dressings for Improving Wound Healing", in Wound Healing—New Insights into Ancient Challenges. Alexandrescu, V. (Ed.). IntechOpen, 2016, 373-398.

Nongonierma, Alice B., et al., "Strategies for the release of dipeptidyl peptidase IV (DPP-IV) inhibitory peptides in an enzymatic hydrolyzate of of α-lactalbumin", Food & Function,7(8): 3437-3443, 2016 (Abstract only).

Okubo, Brunna M., et al., "Evaluation of an antimicrobial L-amino acid oxidase and peptide derivatives from Bothropoides mattogrosensis pitviper venom", PLoS One. 7(3):e33639, 2012.

* cited by examiner

PROBIOTIC MOLECULES FOR REDUCING PATHOGEN VIRULENCE

FIELD

The present invention relates to probiotic molecules. More specifically, the present invention is, in aspects, concerned with probiotic molecules, compositions comprising the probiotic molecules, and various methods and uses of the probiotic molecules.

BACKGROUND

A small biopeptide produced by *Lactobacillus* species has been shown to be effective against enterohemorrhagic *Escherichia coli* infection [Medellin-Peña et al., 2009]. It was shown to influence and down-regulate the transcription of *E. coli* genes involved in colonization and quorum sensing and was able to prevent the adherence of the *E. coli* to host epithelial cells [Medellin-Pena and Griffiths, 2009 "Effect of molecules secreted by *Lactobacillus acidophilus* strain La-5 on *Escherichia coli* O157:H7 colonization.", APPL. ENVIRON. MICROBIOL., 75(4):1165-1172]. It was demonstrated that the biopeptide influenced the *E. coli* type Ill secretion system (T3SS) and was able to interfere with quorum sensing (QS) signalling system and thus resulted in a down-regulation of virulence genes [Medellin-Peña et al., 2007, "Probiotics affect virulence-related gene expression in *Escherichia coli* O157:H7.", APPL. ENVIRON. MICROBIOL., 73:4259-4267; Medellin-Pena and Griffiths, 2009, "Effect of molecules secreted by *Lactobacillus acidophilus* strain La-5 on *Escherichia coli* O157:H7 colonization.", APPL. ENVIRON. MICROBIOL., 75(4):1165-1172].

International Patent Application Publication No. WO 2009/155711 describes isolated and characterized molecules derived from probiotic bacteria from the genera *Lactobacillus, Lactococcus, Streptococcus* or *Bifidobacterium* for use in compositions and methods for the treatment and/or prevention of infection by harmful pathogenic bacteria such as *Salmonella* or *E. coli*. The isolated molecules can also be used in nutritional or medical food products which provide probiotics to the gastrointestinal tract of a mammal.

International Patent Application Publication No. WO 2015/021530 describes molecules derived from probiotic bacteria that are provided for use in compositions and methods for the treatment and/or prevention of infection by pathogenic viruses. The isolated molecules can also be used in nutritional or medical food products which provide probiotics to the gastrointestinal tract of a mammal.

There is a need for alternative therapies to overcome or mitigate at least some of the deficiencies of the prior art, and/or to provide a useful alternative.

DESCRIPTION OF THE DRAWINGS

The present invention will be further understood from the following description with reference to the Figures, in which.

SUMMARY

Figure 1:
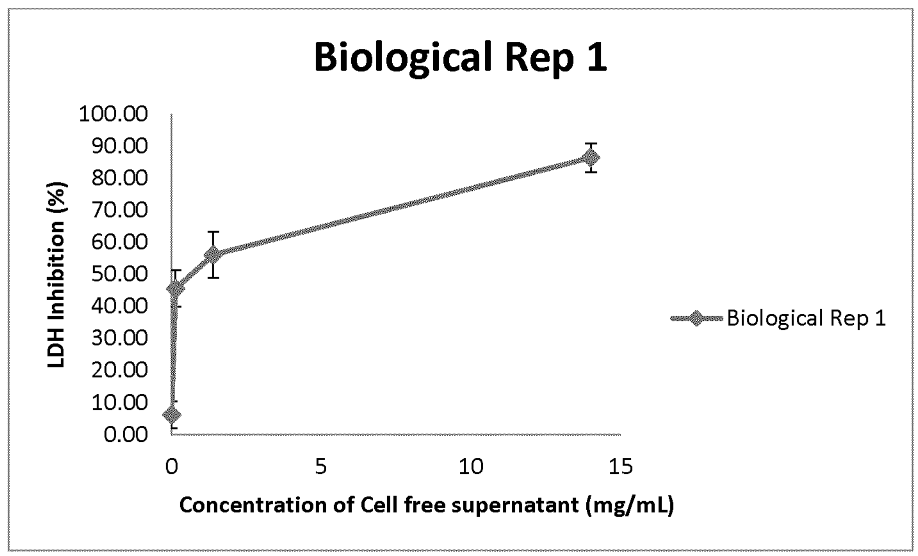
FIG. 1 shows a lactate dehydrogenase cell toxicity assay. Dose response curve of cell toxicity inhibition with cell free supernatant. Error bars represent standard deviation.

In accordance with an aspect, there is provided a peptide for preventing and/or treating a non-enteric infection in a subject and/or for reducing the virulence of a non-enteric infection in a subject, the peptide derived from probiotic bacteria.

In an aspect, the probiotic bacteria is selected from *Lactobacillus, Lactococcus, Streptococcus, Bifidobacterium, Pediococcus*, and combinations thereof.

In an aspect, the *Lactobacillus* is selected from *Lactobacillus acidophilus* (La-5), *Lactobacillus fermentum, Lactobacillus rhamnosus, Lactobacillus reuteri, Lactobacillus helveticus*, and *Lactobacillus plantarum.*

In an aspect, the *Lactococcus* is *Lactococcus lactis.*

In an aspect, the *Bifidobacterium* is selected from *Bifidobacterium longum, Bifidobacterium bifidum, Bifidobacterium infantis, Bifidobacterium* crudilactis and mixtures thereof.

In an aspect, the *Streptococcus* is *Streptococcus* thermophiles.

In an aspect, the peptide is effective against an infection selected from the group consisting of a urinary tract infection, a vaginal infection, a respiratory tract infection, a stomach infection, a biofilm-producing infection, mastitis, a skin infection, and an oral infection.

In an aspect, the peptide is effective against *E. coli*, UPEC, *Haemophilus influenzae, Streptococcus pyogenes, Streptococcus pneumoniae Pseudomonas aeruginosa, Staphylococcus aureus, Helicobacter pylori*, Methicillin-Resistant *Staphylococcus aureus* (MRSA), Porphyrmonas *gingivalis, Prevotella intermedia*, S. saprophytic, Klebiessa, *Enterobacter, Proteus* mirabillis, Enterococci, *Clostridium, Klebsiella*, or *Proteus.*

In an aspect, the peptide is effective against biofilms.

In an aspect, the peptide is further combined with one or more of an antiviral, a sugar source, an edible food product, a nutritional supplement and ingestible liquid.

In an aspect, the peptide is concentrated from a cell-free supernatant or fraction thereof.

In an aspect, the peptide is provided as a dried culture fraction, such as lyophilized or spray-dried.

In an aspect, the dried culture fraction is a cell-free supernatant.

In an aspect, the peptide comprises or consists of a sequence selected from YPVEPF, YPPGGP, YPPG, NQPY, and combinations thereof.

In an aspect, the peptide comprises or consists of the sequence YPPGGP.

In accordance with an aspect, there is provided a composition comprising the peptide described herein.

In an aspect, the composition is a food product, beverage product, health product, medicament, or nutritional supplement.

In an aspect, the composition comprises live probiotic bacteria from which the peptides are derived.

In an aspect, the composition comprises live probiotic bacteria other than the bacteria from which the peptides are derived.

In an aspect, the peptides in the composition are purified.

In accordance with an aspect, there is provided a method of treating and/or preventing a non-enteric infection in a subject and/or for reducing the virulence of a non-enteric infection in a subject, the method comprising administering the peptide or the composition described herein to a subject in need thereof.

In an aspect, the non-enteric infection is selected from the group consisting of a urinary tract infection, a vaginal infection, a respiratory tract infection, a stomach infection, a biofilm-producing infection, mastitis, a skin infection, and an oral infection.

In an aspect, the non-enteric infection is caused by a species selected from the group consisting of *E. coli*, UPEC, *Haemophilus influenzae, Streptococcus pyogenes, Streptococcus pneumoniae Pseudomonas aeruginosa, Staphylococcus aureus, Helicobacter pylori*, Methicillin-Resistant *Staphylococcus aureus* (MRSA), Porphyrmonas *gingivalis, Prevotella intermedia*, S. saprophytic, Klebiessa, *Enterobacter, Proteus* mirabillis, Enterococci, *Clostridium, Klebsiella*, and *Proteus*.

In accordance with an aspect, there is provided a method of reducing antibiotic resistance, comprising administering the peptides described herein to a subject in need thereof.

In an aspect, the method is for reducing antibiotic resistance of MRS.

In accordance with an aspect, there is provided a method of treating MRS, comprising administering the peptides described herein to a subject in need thereof.

In accordance with an aspect, there is provided a method of preventing or disrupting and/or penetrating biofilms, comprising administering the peptides described herein.

In accordance with an aspect, there is provided a method of treating a wound, comprising administering the peptides described herein.

In accordance with an aspect, there is provided a method of reducing attachment of a non-enteric pathogen to tissue of a subject, comprising administering the peptides described herein.

In accordance with an aspect, there is provided an inert object comprising the peptides described herein.

In an aspect, the inert object is a stent, catheter, or wound dressing comprising the probiotic molecules, which are released from the object over a period of time.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from the detailed description.

DETAILED DESCRIPTION

Probiotic molecules have been described for use in treating gastrointestinal infections. Without wishing to be bound by theory, it is believe that molecules described in International Patent Application Publication Nos. WO 2009/155711 and WO 2015/021530 interfere with the quorum sensing (QS) system of type Ill secretion system (T3SS) pathogens and previous work has shown that the probiotic molecules can cause a down-regulation of virulence genes for a variety of enteric pathogens. The cell free extract of a *L. acidophilus* strain was capable of interfering with quorum sensing in *Clostridium difficile* and was able to down-regulate *C. difficile* virulence genes [Yun et al., 2014]. Cell free extracts of *Lactobacillus* and *Bifidobacterium* strains inhibited the growth of *Campylobacter jejuni* and down-regulated flaA sigma 28 promoter and were able to down-regulate expression of ciaB and flaA genes in *Campylobacter jejuni* [Ding et al., 2005, Mundi et al., 2013]. The probiotic molecules produced by *Lactobacillus* were also found to affect the virulence of *Salmonella* and was shown to mainly target virulence genes involved in T3SS [Sharma 2014]. A field trial carried out in 2015 tested the probiotic molecules in vivo with weaned piglets and was found to have a significant effect in decreasing the severity and cases of diarrhea [University of Guelph/MicroSintesis, 2015].

It has now been found that this mode of action is also effective in down-regulating the effects of virulence genes that are regulated by quorum sensing in other types of pathogens and infections, not just enteric pathogens. Further, these peptides in aspects are capable of overcoming drug resistance at least in part, in other aspects are capable of reducing drug resistance, in other aspects, are capable of treating and/or preventing and/or reducing the virulence of infections caused by drug resistant bacteria, and in other aspects, are capable of potentiating the effects of antibiotics on bacteria and/or drug resistant bacteria.

Definitions

Unless defined otherwise, technical and scientific terms used herein have the same meaning as commonly understood by one of ordinary skill in the art to which this invention belongs. See, e.g. Singleton et al., Dictionary of Microbiology and Molecular Biology 2nd ed., J. Wiley & Sons (New York, N.Y. 1994); Sambrook et al., Molecular Cloning. A Laboratory Manual, Cold Springs Harbor Press (Cold Springs Harbor, N Y 1989), each of which are incorporated herein by reference. For the purposes of the present invention, the following terms are defined below.

By "derived," it is meant that probiotic molecules are either directly or indirectly produced by the probiotic bacteria. For example, the probiotic bacteria may secrete the probiotic molecules directly into the culture medium. In other aspects, the molecules can be formed indirectly within the culture medium, for example, by being cleaved from longer peptides.

"Variants" of the sequences described herein are biologically active sequences that have a peptide sequence that differs from the sequence of a native or wild-type sequence, by virtue of an insertion, deletion, modification and/or substitution of one or more amino acids within the native sequence. Such variants generally have less than 100% sequence identity with a native sequence. Ordinarily, however, a biologically active variant will have an amino acid sequence with at least about 70% sequence identity with the sequence of a corresponding naturally occurring sequence, typically at least about 75%, more typically at least about 80%, even more typically at least about 85%, even more typically at least about 90%, and even more typically of at least about 95%, 96%, 97%, 98%, or 99% sequence identity. The variants nucleotide fragments of any length that retain a biological activity of the corresponding native sequence. Variants also include sequences wherein one or more amino acids are added at either end of, or within, a native sequence. Variants also include sequences where a number of amino acids are deleted and optionally substituted by one or more different amino acids.

"Percent sequence identity" is defined herein as the percentage of amino acid residues in the candidate sequence that are identical with the residues in the sequence of interest after aligning the sequences and introducing gaps, if necessary, to achieve the maximum percent sequence identity, and not considering any conservative substitutions as part of the sequence identity. None of 5', 3', or internal extensions, deletions or insertions into the candidate sequence shall be construed as affecting sequence identity or homology. Methods and computer programs for the alignment are well known in the art, such as "BLAST".

"Active" or "activity" for the purposes herein refers to a biological activity of a native or naturally-occurring probiotic molecule, wherein "biological" activity refers to a biological function (either inhibitory or stimulatory) caused by a native or naturally-occurring probiotic molecule.

Thus, "biologically active" or "biological activity" when used in conjunction with the probiotic molecules described herein refers to probiotic molecule or amino acid sequence that exhibits or shares an effector function of the native probiotic molecule or sequence. For example, the probiotic molecules described herein have the biological activity of preventing, inhibiting, or treating an infection in an animal.

"Biologically active" or "biological activity" when used in conjunction with variant sequences means that the variant sequences exhibit or share an effector function of the parent sequence. The biological activity of the variant sequence may be increased, decreased, or at the same level as compared with the parent sequence.

"Isolated" refers to a molecule that has been purified from its source or has been prepared by recombinant or synthetic methods and purified. Purified probiotic molecules are substantially free of other amino acids.

"Substantially free" herein means less than about 5%, typically less than about 2%, more typically less than about 1%, even more typically less than about 0.5%, most typically less than about 0.1% contamination with other source amino acids. An "essentially pure" probiotic molecule composition means a composition comprising at least about 90% by weight of the probiotic molecule, based on total weight of the composition, typically at least about 95% by weight, more typically at least about 90% by weight, even more typically at least about 95% by weight, and even more typically at least about 99% by weight of nucleotide, based on total weight of the composition.

As used herein, "treatment" or "therapy" is an approach for obtaining beneficial or desired clinical results. For the purposes described herein, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" and "therapy" can also mean prolonging survival as compared to expected survival if not receiving treatment or therapy. Thus, "treatment" or "therapy" is an intervention performed with the intention of altering the pathology of a disorder. Specifically, the treatment or therapy may directly prevent, slow down or otherwise decrease the pathology of a disease or disorder such as an infection, or may render the infection more susceptible to treatment or therapy by other therapeutic agents.

The terms "therapeutically effective amount", "effective amount" or "sufficient amount" mean a quantity sufficient, when administered to a subject, including a mammal, for example a human, to achieve a desired result, for example an amount effective to treat an infection. Effective amounts of the probiotic molecules described herein may vary according to factors such as the disease state, age, sex, and weight of the subject. Dosage or treatment regimes may be adjusted to provide the optimum therapeutic response, as is understood by a skilled person.

Moreover, a treatment regime of a subject with a therapeutically effective amount may consist of a single administration, or alternatively comprise a series of applications. The length of the treatment period depends on a variety of factors, such as the severity and/or site of the disease, the age of the subject, the concentration of the agent, the responsiveness of the patient to the agent, or a combination thereof. It will also be appreciated that the effective dosage of the agent used for the treatment may increase or decrease over the course of a particular treatment regime. Changes in dosage may result and become apparent by standard diagnostic assays known in the art. The probiotic molecules described herein may, in aspects, be administered before, during or after treatment with conventional therapies for the disease or disorder in question, such as an infection.

The term "subject" as used herein refers to any member of the animal kingdom, including birds, fish, invertebrates, amphibians, mammals, and reptiles. Typically, the subject is a human or non-human vertebrate. Non-human vertebrates include livestock animals, companion animals, and laboratory animals. Non-human subjects also specifically include non-human primates as well as rodents. Non-human subjects also specifically include, without limitation, poultry, chickens, horses, cows, pigs, goats, dogs, cats, guinea pigs, hamsters, mink, rabbits, crustaceans, and molluscs. Typically the subject is poultry or a mammal. The term "mammal" refers to any animal classified as a mammal, including humans, other higher primates, domestic and farm animals, and zoo, sports, or pet animals, such as dogs, cats, cattle, horses, sheep, pigs, goats, rabbits, etc. Typically, the mammal is human.

Administration "in combination with" one or more further therapeutic agents includes simultaneous (concurrent) and consecutive administration in any order.

The term "pharmaceutically acceptable" means that the compound or combination of compounds is compatible with the remaining ingredients of a formulation for pharmaceutical use, and that it is generally safe for administering to humans according to established governmental standards, including those promulgated by the United States Food and Drug Administration.

"Carriers" as used herein include pharmaceutically acceptable carriers, excipients, or stabilizers that are nontoxic to the cell or subject being exposed thereto at the dosages and concentrations employed. Often the pharmaceutically acceptable carrier is an aqueous pH buffered solution. Examples of pharmacologically acceptable carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, and dextrins; chelating agents such as EDTA; sugar alcohols such as mannitol and sorbitol; salt-forming counterions such as sodium; and/or nonionic surfactants such as TWEEN™, polyethylene glycol (PEG), and PLURONICS™.

A "liposome" is a small vesicle composed of various types of lipids, phospholipids and/or surfactant which is useful for delivery of an agent, such as the probiotic molecules described herein, to a subject, such as a mammal. The components of the liposome are commonly arranged in a bilayer formation, similar to the lipid arrangement of biological membranes.

In understanding the scope of the present application, the articles "a", "an", "the", and "said" are intended to mean that there are one or more of the elements. Additionally, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

It will be understood that any aspects described as "comprising" certain components may also "consist of" or "consist essentially of," wherein "consisting of" has a closed-ended or restrictive meaning and "consisting essentially of" means including the components specified but excluding other components except for materials present as impurities, unavoidable materials present as a result of processes used to provide the components, and components added for a purpose other than achieving the technical effect of the invention. For example, a composition defined using the phrase "consisting essentially of" encompasses any known pharmaceutically acceptable additive, excipient, diluent, carrier, and the like. Typically, a composition consisting essentially of a set of components will comprise less than 5% by weight, typically less than 3% by weight, more typically less than 1% by weight of non-specified components.

It will be understood that any component defined herein as being included may be explicitly excluded from the claimed invention by way of proviso or negative limitation. For example, in aspects, enteric infections, such as enteric bacterial and/or enteric viral infections, are explicitly excluded from the compositions and methods described herein. In other aspects, the molecules described herein are not bacteriocins.

In addition, all ranges given herein include the end of the ranges and also any intermediate range points, whether explicitly stated or not.

Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

Probiotic Molecules and Compositions Comprising Probiotic Molecules

The present invention provides probiotic molecules isolated from probiotic bacteria and further culture fractions, such as a cell-free supernatant, of the bacteria that can minimize, inhibit, treat, and/or prevent infection in subjects, typically non-enteric infections. In particular, the molecule(s) may be derived from one or more bacterial species selected from the group consisting of the genera *Aerococcus, Bacillus, Bacteroides, Bifidobacterium, Clostridium, Enterococcus, Fusobactehum, Lactobacillus, Lactococcus, Leuconostoc, Melissococcus, Micrococcus, Pediococcus, Peptostrepococcus, Propionibacterium, Staphylococcus, Streptococcus* and *Weissella*. Specific probiotically active lactic acid bacterial species include *Enterococcus faecalis, Enterococcus faecium, Lactobacillus acidophilus, Lactobacillus alimentarius, Lactobacillus casei* Shirota, *Lactobacillus casei* subsp. *paracasei, Lactobacillus casei* subsp. *casei, Lactobacillus casei, Lactobacillus crispatus, Lactobacillus curvatus, Lactobacillus* delbruckii subsp. *lactis, Lactobacillus delbrueckii* subsp. *bulgaricus, Lactobacillus farciminus, Lactobacillus fermentum, Lactobacillus gasseri, Lactobacillus helveticus, Lactobacillus johnsonii, Lactobacillus paracasei* subsp. *paracasei, Lactobacillus rhamnosus, Lactobacillus plantarum, Lactobacillus reuteri, Lactobacillus rhamnosus, Lactobacillus sake, Lactococcus lactis, Lactocoocus lactis* subsp. *cremoris, Streptococcus faecalis, Streptococcus faecium, Streptococcus salivarius* and *Streptococcus thermophilus*. Further examples comprise probiotically active *Bifidobacterium* species including *Bifidobacterium infantis, Bifidobacterium adolescentis, Bifidobacterium bifidum, Bifidobacterium longum, Bifidobacterium lactis, Bifidobacterium animalis* and *Bifidobacterium breve*.

Further bacterial species can be selected from the group consisting of probiotically active *Paenibacillus lautus, Bacillus coagulans, Bacillus licheniformis, Bacillus subtilis, Micrococcus varians, Pediococcus acidilactici, Pediococcus pentosaceus, Pediococcus* acidi-lactici, *Pediococcus halophilus, Staphylococcus carnosus* and *Staphylococcus* xylosus, as well as the microorganism *Lactobacillus casei* ssp. *rhamnosus* strain LC-705, DSM 7061 described in EP publication No. 0576780, and described as *Lactobacillus rhamnosus* LC-705, DSM 7061 in U.S. Pat. No. 5,908,646, alone or in combination with a bacterium of the genus *Propionibacterium* or another strain of *Lactobacillus casei*.

Specific probiotic bacterial strains that may produce the molecules described herein are, in aspects, selected from the group of strains consisting of: *Bifidobacterium animalis* strain DSM15954, *Bifidobacterium longum* subsp. *infantis* strain DSM15953, *Bifidobacterium longum* subsp. *longum* strain DSM15955, *Enterococcus faecium* strain DSM15958, *Lactobacillus acidophilus* strain DSM13241 (La-5), *Lactobacillus delbrueckii* subsp. *bulgaricus* strain DSM15956, *Lactobacillus helveticus* strain DSM14998, *Lactobacillus helveticus* strain DSM14997, *Lactococcus lactis* strain DSM14797, *Streptococcus thermophilus* strain DSM15957, *Lactobacillus fermentum* strain ATCC55845 and *Lactobacillus rhamnosus* strain ATCC55826.

In typical aspects, the molecules are derived from *Lactobacillus acidophilus* (La-5) as well as from strains of *Pediococcus*, strains of *Bifidobacterium* such as but not limited to *Bifidobacterium longum, Bifidobacterium bifidum, Bifidobacterium infantis*, and *Bifidobacterium* crudilactis, and also from *Lactobacillus fermentum, Lactobacillus rhamnosus, Lactobacillus helveticus, Lactobacillus plantarum, Lactococcus lactis*, and *Streptococcus thermophilus*.

The probiotic molecules are now shown to be effective against non-enteric pathogens and novel molecules have been identified that are effective against enteric and non-enteric pathogens. The probiotic molecules described herein include the molecules described in International Patent Application Publication Nos. WO 2009/155711 and WO 2015/021530, which are each incorporated herein by reference in their entirety.

In aspects, the probiotic molecules are small molecules, typically proteinaceous, that are temperature resistant (can be heated, frozen and thawed and still exhibit activity), are stable for long periods of time frozen (over two years), can be produced readily in large volumes (for example about 2 mg/L), and can be dried by methods such as lyophilisation and/or spray-drying. Typically, the molecules are peptides.

The molecules can be incorporated into a variety of substances for administration to a subject such as any type of animal and humans. For example, the molecules can be incorporated into any type of food product, nutritional supplement or beverage for animal or human consumption.

As a therapeutic, the probiotic molecules described herein can be administered in a manner to an animal or human for the effective treatment of infection. As a therapeutic or prophylactic, the treatment can be in conjunction with other therapies as is desired. In another embodiment, the probiotic molecules described herein can be used in compositions and in methods in addition to use of whole probiotic bacteria. Alternatively, whole probiotic bacteria can be used alone, provided the bacteria are cultured and/or used such that the molecules are produced in the culture medium in a therapeutically effective amount.

In aspects the probiotic molecules are derived from probiotic bacteria, such as *Lactobacillus acidophilus* (La-5), wherein the molecule comprises one or more of the following amino acid sequences: YPVEPF, YPPGGP, YPPG, and NQPY. Typically, the molecule comprises the following amino acid sequence: YPPGGP. It is understood by one of skill in the art that these sequences can be altered by deletion, substitution or insertion so long as the activity of the molecules is not substantially reduced. The sequences can further have insertions, substitutions, or deletions of one or more of the amino acid residues. Furthermore, the molecules described herein may further be altered with glycosylation, unglycosylation, organic and inorganic salts and covalently modified. Also encompassed are molecules modified to increase in vivo half-life, e.g., PEGylated. Possible but non-limiting modifications to the molecules described herein include modifications comprising combinations of amino acid substitutions together with a deletion of one or more amino acids or the addition of one or more amino acids.

In a generalized aspect, the molecules described herein can be provided in a therapeutically effective amount alone or within a composition and in amounts that may vary according to factors such as the infection state/health, age, sex, and weight of the recipient. Dosage regimes may be adjusted to provide the optimum therapeutic response and may be at the discretion of the attending physician or veterinarian. For example, several divided doses may be administered daily or on at periodic intervals, and/or the dose may be proportionally reduced as indicated by the exigencies of the therapeutic situation. The amount of the molecule for administration will depend on the route of administration, time of administration and may be varied in accordance with individual subject responses. Suitable administration routes are, for example, via the topical, oral, rectal or parenteral (e.g., intravenous, subcutaneous or intramuscular) route. In addition, the molecules can be incorporated into polymers allowing for sustained release, the polymers being implanted in the vicinity of where delivery is desired, for example, at the site of an infection, or the polymers can be implanted, for example, subcutaneously or intramuscularly or delivered intravenously or intraperitoneally to result in systemic delivery of the molecules described herein.

The molecules described herein can be administered in the form of, for example, a tablet, a capsule, a lozenge, a cachet, a solution, a suspension, an emulsion, a powder, an aerosol, a suppository, a spray, a pastille, an ointment, a cream, a paste, a foam, a gel, a tampon, a pessary, a granule, a bolus, a mouthwash, or a transdermal patch. The molecules may be administered as a cell-free supernatant, which, in aspects is a cell-free supernatant concentrate. The concentrate may be in liquid or powder form.

The formulations include those suitable for oral, rectal, nasal, inhalation, topical (including dermal, transdermal, buccal and sublingual), vaginal, parenteral (including subcutaneous, intramuscular, intravenous, intradermal, intraocular, intratracheal, and epidural), intramammary, or inhalation administration. The formulations can conveniently be presented in unit dosage form and can be prepared by conventional pharmaceutical techniques. Such techniques include the step of bringing into association the active ingredient and a pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion, etc.

A tablet may be made by compression or molding, optionally with one or more accessory ingredients. Compressed tablets may be prepared by compressing, in a suitable machine, the molecules described herein in a free-flowing form such as a powder or granules, optionally mixed with a binder, lubricant, inert diluent, preservative, surface-active and/or dispersing agent. Molded tablets may be made by molding, in a suitable machine, a mixture of the powdered compound moistened with an inert liquid diluent. The tablets may optionally be coated or scored and may be formulated so as to provide a slow or controlled release of the active ingredient therein.

Formulations suitable for topical administration in the mouth include lozenges comprising the ingredients in a flavored base, typically sucrose and acacia or tragacanth; pastilles comprising the active ingredient in an inert base such as gelatin and glycerin, or sucrose and acacia; and mouthwashes comprising the ingredient to be administered in a suitable liquid carrier.

Formulations suitable for topical administration to the skin may be presented as ointments, creams, gels, or pastes comprising the ingredient to be administered in a pharmaceutical acceptable carrier. In one embodiment the topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tampons, creams, gels, pastes, foams or spray formulations containing, in addition to the active ingredient, ingredients such as carriers as are known in the art to be appropriate.

Formulations suitable for inhalation may be presented as mists, dusts, powders or spray formulations containing, in addition to the active ingredient, ingredients such as carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. Formulations suitable for parenteral administration include particulate preparations of the anti-angiogenic agents, including, but not limited to, low-micron, or nanometer (e.g. less than 2000 nanometers, typically less than 1000 nanometers, most typically less than 500 nanometers in average cross section) sized particles, which particles are comprised of the molecules described herein alone or in combination with accessory ingredients or in a polymer for sustained release. The formulations may be presented in unit-dose or multi-dose containers, for example, sealed ampules and vials, and may be stored in freeze-dried (lyophilized) conditions requiring only the addition of a sterile liquid carrier, for example, water for injections, immediately prior to use. Extemporaneous injection solutions and suspensions may be prepared from sterile powders, granules and tablets of the kinds previously described.

Compositions comprising the molecules described herein may comprise about 0.00001% to about 99% by weight of the active and any range there-in-between. For example, typical doses may comprise from about 0.1 μg to about 100 μg of the molecules described herein per 300 mg dose, such as about 0.5 μg, about 1 μg, about 2 μg, about 3 μg, about 4 μg, about 5 μg, about 6 μg, about 7 μg, about 8 μg, about 9 μg, about 10 μg, about 25 μg, about 50 μg, or about 75 μg per 300 mg dose, such as from about 0.1 μg to about 10 μg, or from about 1 μg to about 5 μg, or from about 1 μg to about 2 μg per 300 mg dose (and all related increments and percentages by weight).

The probiotic molecules may be administered over a period of hours, days, weeks, or months, depending on several factors, including the severity of the infection being treated, whether a recurrence of the infection is considered likely, or to prevent infection, etc. The administration may be constant, e.g., constant infusion over a period of hours, days, weeks, months, etc. Alternatively, the administration may be intermittent, e.g., the molecules may be administered once a day over a period of days, once an hour over a period of hours, or any other such schedule as deemed suitable.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in "Handbook of Pharmaceutical Additives" (compiled by Michael and Irene Ash, Gower Publishing Limited, Aldershot, England (1995)). On this basis, the compositions include, albeit not exclusively, solutions of the substances in association with one or more pharmaceutically acceptable vehicles or diluents, and may be contained in buffered solutions with a suitable pH and/or be iso-osmotic with physiological fluids. In this regard, reference can be made to U.S. Pat. No. 5,843,456 (the entirety of which is incorporated herein by reference).

Pharmaceutically acceptable carriers are well known to those skilled in the art and include, for example, sterile saline, lactose, sucrose, calcium phosphate, gelatin, dextrin, agar, pectin, peanut oil, olive oil, sesame oil and water. Furthermore the pharmaceutical composition may comprise one or more stabilizers such as, for example, carbohydrates including sorbitol, mannitol, starch, sucrose, dextrin and glucose, proteins such as albumin or casein, and buffers like alkaline phosphates.

In another non-limiting aspect, administration of the probiotic molecules can be accomplished by any method likely to introduce the molecules into the digestive tract, such as orally or rectally, after which the probiotic molecules enter the bloodstream. The bacteria producing the probiotic molecules and/or the isolated probiotic molecules can be mixed with a carrier and applied to liquid or solid feed or to drinking water. The carrier material should be non-toxic to the animal. The bacteria producing the probiotic molecules and/or the isolated probiotic molecules can also be formulated into a composition provided as an inoculant paste to be directly injected into an animal's mouth. The formulation can include added ingredients to improve palatability, improve shelf-life, impart nutritional benefits, and the like. If a reproducible and measured dose is desired, the molecules can be administered by a rumen cannula, as described herein. The amount of the molecules isolated from probiotic bacteria to be administered is governed by factors affecting efficacy. By monitoring the infection before, during and after administration of the probiotic molecules from probiotic bacteria, those skilled in the art can readily ascertain the dosage level needed to reduce the amount of infection carried by the animals. The molecules from one or more strains of probiotic bacteria can be administered together. A combination of strains can be advantageous because individual animals may differ as to the strain which is most persistent in a given individual.

The methods for administering the probiotic molecules are essentially the same, whether for prevention or treatment. Therefore, the need to first determine whether a pathogenic infection is being carried by the animals is removed. By routinely administering an effective dose to all the animals of a herd, the risk of contamination by a pathogenic infection can be substantially reduced or eliminated by a combination of prevention and treatment.

It is understood by one of skill in the art that the isolated molecules and culture fractions containing such, can be used in conjunction with known therapies for prevention and/or treatment of infections in subjects. It is also understood that compositions of the probiotic molecules described herein, whether isolated or in a culture fraction or in conjunction with probiotic bacteria, can also be used in conjunction (formulated with) with a sugar source such as for example glucose in amounts of up to about 0.01% to about 0.1% or more by weight of the composition.

It is also understood that although the compositions described herein may be directly ingested or used as an additive in conjunction with foods, it will be appreciated that they may be incorporated into a variety of foods and beverages including but not limited to yoghurts, ice creams, cheeses, baked products such as bread, biscuits and cakes, dairy and dairy substitute foods, confectionery products, edible oil compositions, spreads, breakfast cereals, juices, meats, produce, and the like. Within the scope of the term "foods" are to be included in particular food likely to be classified as functional foods, i.e. "foods that are similar in appearance to conventional foods and are intended to be consumed as part of a normal diet, but have been modified to physiological roles beyond the provision of simple nutrient. Similarly, the compositions described herein may be presented in dosage forms such as in a capsule or a dried and compressed tablet or rectal or vaginal suppository, or as an aerosol or inhaler. Again, amounts of the active probiotic molecules will vary depending on the particular food or beverage and may contain any amount up to about 100% of the product, especially when formulated as an ingestible capsule/tablet.

It is also understood by one of skill in the art that the molecules described herein, whether isolated or provided as within a culture fraction, can be combined with the use of probiotic bacteria in methods of treatment or for nutritional supplementation. In particular aspects, the molecules described herein may be combined with live probiotic bacteria of the species from which the molecules are derived. In other aspects, these bacterial species may be excluded from the compositions. In other aspects, the molecules described herein may be combined with live probiotic bacteria of a species that does not produce the molecules.

Methods of Use

Unexpectedly, it has been found that the probiotic molecules described herein, whether administrated in isolated form or in the form of bacteria from which the probiotic molecules are derived, find use in treating infections, in aspects enteric or non-enteric infections, a number of which are specifically described below.

In particular aspects, the molecules described herein interact synergistically with one another and/or with antibiotics or other anti-infective agents to treat and/or prevent an enteric or non-enteric infection and/or to reduce the virulence of an enteric or non-enteric infection, including reducing antibiotic resistance and/or increasing the sensitivity of a particular pathogenic microorganism to a conventional treatment such as an antibiotic.

Urinary Tract Infections

Urinary tract infections (UTIs) are one of the most frequently acquired bacterial infections in humans, with *E. coli* being responsible for 90% of all UTIs and affecting an estimated 11.3 million women every year [Marrs et al., 2005]. *Lactobacillus* strains, which dominate the flora found in the vaginas of healthy women, spread from the rectum and perineum and form a barrier in the vagina to block entry by uropathogens. The concept of artificially boosting the number of lactobacilli through probiotics has long been theorized but only recently shown to be effective [Reid and Bruce, 2005]. A variety of studies have shown a positive effect of probiotic strains of *Lactobacillus* used to treat UTIs, specifically in preventing re-current UTIs [Bruce et al., 1992; Chrisholm, 2015; Delley et al., 2015; Stapleton et al., 2011]. There is a strong need to find a safe effective and non-antimicrobial treatment for recurrent urinary tract infections [Stapleton et al., 2011].

The most common UTI pathogen is *E. coli* which has virulence regulated by QS and enteric *E. coli* has been previously shown to be less virulent when treated with the probiotic molecules described herein [Medellin-Peña et al., 2007, Medellin-Pena and Griffiths, 2009, incorporated herein by reference in their entirety]. Uropathogenic *E. coli* (UPEC) has many of the same virulence genes activated as enteric *E. coli* and has T3SS. Thus, the probiotic molecules described herein should be effective in reducing the virulence of the UPEC strain [Snyder et al., 2004]. Reid [2000], showed that a strain of *Lactobacillus acidophilus* produced a compound that significantly inhibited the uropathogenic enterococci to adhere to uroepithelial cells. A main gene noted in vivo for UTI is fim genes which are fimbrial protein genes required for attaching to the surface of uroepithelial cells which is required for infection to occur [Snyder et al., 2004]. We will test the regulation of these genes in a UPEC strain for down regulation when exposed to the probiotic molecules described herein to ensure that the biopeptide is effective in reducing the virulence in a uropathogenic strain of *E. coli*.

In other aspects, the probiotic molecules described herein could find use in treating acute cystitis, such as that caused by *E. coli* or *S. saprophyticus*; in treating pyelonephritis, such as that caused by *E. coli, Klebsiella, Enterobacter*, or *Proteus* mirabillis; in treating complicated UTI, such as that caused by *E. coli*, Enterococci, *Klebsiella, Proteus*, or *P. aeruginosa*; or prostatitis, such as that caused by *E. coli*, gram negative bacilli, *Staphylococcus*, or *Enterococcus.*

Bacterial Vaginosis

Another common infection is bacterial vaginosis (BV), which is characterized by a shift in the vaginal flora from a predominance of protective lactobacilli to pathogenic bacteria and accounting for up to 25% of visits to gynecologic clinics [Barrons and Tassone, 2008]. BV increases the risk of HIV infection and increases the risk of low birth weight babies and preterm delivery [Reid and Burton, 2002]. BV cure rates with traditional antibiotics are low and infections recur in up to 50% of women at 6 months [Barrons and Tassone, 2008]. Daily intake of *Lactobacillus* strains resulted in a restoration of a normal vaginal flora in patients with asymptomatic BV [Reid and Burton, 2002]. It was found in the study that the use of *Lactobacillus* strains alone were associated with BV cure rates comparable to those with standard antibiotic therapies [Barrons and Tassone, 2008].

Studies have shown that the use of freeze dried suppositories of probiotic bacteria allows for quicker colonization of the urogenital tract by the probiotic cells [Barrons and Tassone, 2008; Reid and Bruce, 2006]. As the probiotic molecules described herein are resistant to drying methods such as lyophilisation, freeze-dried suppositories are a viable mode of delivery. This would make the probiotic molecules more readily available at the site of infection.

Respiratory Infections

Respiratory infections encompass a wide variety of infections (otitis, pneumonia, pharyngitis) and pathogens including, common strains such as *Haemophilus influenzae, Streptococcus pyogenes, Streptococcus pneumoniae, Pseudomonas aeruginosa*, and *Staphylococcus aureus* [Nagalingam et al, 2013]. Respiratory infections are very serious especially for infants and the elderly, significantly contributing to morbidity and mortality worldwide. Alternative treatments and preventions would be beneficial [Véras de Araujo et al., 2015].

Both lower and upper respiratory tract infections are specifically contemplated herein as being useful for treatment with the molecules described herein. For example, *Streptococcus pyogenes*, a group A *streptococcus* in streptococcal pharyngitis ("strep throat") and/or other throat infections may be treated with the molecules described herein.

Nagalingam et al. suggest that the composition of the sinus microbiome is correlated with disease. The sinus microbiome of patients with chronic rhinosinusitis showed a significant reduction in lactic acid bacteria (LAB) populations as compared to that of healthy individuals [Nagalingam et al., 2013]. They further suggest that supplementation of LAB could be used to protect mucosal surfaces of the respiratory tract against infection, similar to the case with the GI and urogenital tract [Nagalingam et al., 2013]. There is a large body of studies on the effects of probiotic and upper respiratory infections. Two examples have shown that in two very susceptible populations (infants and the elderly) that those orally supplemented with probiotic bacteria were found to have fewer upper respiratory infections (URI) in comparison to control groups [Maldonado et al, 2012; Guillmard et al., 2010].

Most studies utilized oral ingestion of probiotic bacteria, however, nasal sprays have also been effective [Skovberg et al., 2009]. This suggests nasal sprays as another mode of delivery. This would enhance the delivery of the probiotic bacteria to the site of infection.

*Helicobacter pylori* Infection

*Helicobacter pylori* causes chronic gastritis, and is responsible for the development of peptic ulcer disease, and is considered a risk factor in the development of gastric malignancies such as gastric mucosa-associated lymphoid tissue lymphomas and gastric adenocarcinoma [Wang et al., 2004]. Although existing antibiotic treatments are effective, there are concerns over antibacterial resistance. Moreover such drugs can have negative side effects which often lead to discontinuing treatment. For these reasons it is desirable to investigate alternative treatments [Wang et al., 2004]. In their study Wang et al., [2004] found that ingesting probiotic yogurt containing *Lactobacillus* and *Bifidobacterium* strains were able to suppress infection of *H. pylori* in humans [Wang et al., 2004]. In an older study it was found that the supernatant of *Lactobacillus acidophilus* La1 inhibited *H. pylori* growth in vitro and was shown to have a suppressive effect on *H. pylori* in humans [Michetti et al., 1999]. Another study by Canducci et al., has also shown that *L. acidophilus* spent culture supernatant was able to dramatically reduce the viability of *H. pylori* in vitro as well as in vivo [2000]. This strongly suggests that the probiotic bioactivesa produced by *Lactobacillus* strains in the cell free spent media could have a beneficial effect in treating an *H. pylori* infection.

Methicillin-Resistant *Staphylococcus aureus* (MRSA) Infection

Methicillin-Resistant *Staphylococcus aureus* (MRSA) is responsible for many life threatening infections including pneumonia, sepsis, oseomyelitis and endocarditis. Patients are typically colonized for long periods of time with 50% of patients still colonized after one year [Karska-Wysocki, et al., 2010]. MRSA is a biofilm producing pathogen able to adhere to many surfaces. This study demonstrated that *Lactobacillus acidophilus* was able to eliminate 99% of the MRSA cells after a 24 hour incubation. The study links the effect to lactic acid bacteria producing bioactive peptides that inhibit biofilm production [Karska-Wysocki, et al., 2010]. The probiotic molecules described herein have been shown to interfere with QS systems which regulate biofilm production. This could inhibit biofilms and therefore the probiotic molecules may be effective in not only treating MRSA but other antibiotic resistant pathogens.

Oral Health

Scientific studies suggest that probiotics are effective in maintaining oral health and preventing oral disease. For example it has been shown that probiotics can enhance the commensal flora and prevent the colonization of pathogens, preventing gingival inflammation [Iniesta et al., 2012]. There have been several studies that assess the use of Lactobacilli probiotics in oral health. The results indicate that the use of *L. reuteri* containing tablets was associated with a significant reduction in *Prevotella intermedia* in saliva as well as in the counts of periodontal pathogens, such as *P. gingivalis* [Iniesta et al., 2012]. The results indicate that oral administration of *L. reuteri* lozenges could be useful in conjunction with scaling and root planing in chronic periodontitis [Teughels et al., 2013].

Porphyrmonas *gingivalis* is the common pathogen responsible for periodontitis. A probiotic *Lactobacillus* strain significantly decreased the number of *P. gingivalis* [Matsuoka and Koga, 2014]. The examples show that the use of *Lactobacillus* probiotic bacteria can interfere with the pathogen's adherence and that colonization can lead to a significant health benefit.

From the above, it is evident that the probiotic molecules described herein can find use in the treatment of a wide variety of pathogens, including bacteria, viruses, yeast, fungus, and parasites. In aspects, the pathogen is non-enteric and/or the infection is at a non-enteric site.

For example, the probiotic molecules described herein may be useful in treating a bacterial infection from a genus selected from the group consisting of *Abiotrophia, Achromobacter, Acidaminococcus, Acidovorax, Acinetobacter, Actinobacillus, Actinobaculum, Actinomadura, Actinomyces, Aerococcus, Aeromonas, Afipia, Agrobacterium, Alcaligenes, Alloiococcus, Alteromonas, Amycolata, Amycolatopsis, Anaerobospirillum, Anaerorhabdus, "Anguillina", Arachnia, Arcanobacterium, Arcobacter, Arthrobacter, Atopobium, Aureobacterium, Bacillus, Bacteroides, Balneatrix, Bartonella, Bergeyella, Bifidobacterium, Bilophila, Branhamella, Borrelia, Bordetella, Brachyspira, Brevibacillus, Brevibacterium, Brevundimonas, Brucella, Burkholderia, Buttiauxella, Butyrivibrio, Calymmatobacterium, Campylobacter, Capnocytophaga, Cardiobacterium, Catonella, Cedecea, Cellulomonas, Centipeda, Chlamydia, Chlamydophila, Chromobacterium, Chyseobacterium, Chryseomonas, Citrobacter, Clostridium, Collinsella, Comamonas, Corynebacterium, Coxiella, Cryptobacterium, Delflia, Dermabacter, Dermatophilus, Desulfomonas, Desulfovibrio, Dialister, Dichelobacter, Dolosicoccus, Dolosigranulum, Edwardsiella, Eggerthella, Ehrlichia, Eikenella, Empedobacter, Enterobacter, Enterococcus, Erwinia, Erysipelothrix, Escherichia, Eubacterium, Ewingella, Exiguobacterium, Facklamia, Filif actor, Flavimonas, Flavobacterium, Flexispira, Francisella, Fusobacterium, Gardnerella, Gemella Globicatella, Gordona, Haemophilus, Hafnia, Helicobacter, Helococcus, Holdemania, Ignavigranum, Johnsonella, Kingella, Klebsiella, Kocuria, Koserella, Kurthia, Kytococcus, Lactobacillus, Lactococcus, Lautropia, Leclercia, Legionella, Leminorella, Leptospira, Leptotrichia, Leuconostoc, Listeria, Listonella, Megasphaera, Methylobacterium, Microbacterium, Micrococcus, Mitsuokella, Mobiluncus, Moellerella, Moraxella, Morganella, Mycobacterium, Mycoplasma, Myroides, Neisseria, Nocardia, Nocardiopsis, Ochrobactrum, Oeskovia, Oligella, Orientia, Paenibacillus, Pantoea, Parachlamydia, Pasteurella, Pediococcus, Peptococcus, Peptostreptococcus, Photobacterium, Photorhabdus, Plesiomonas Porphyrimonas, Prevotella, Propionibacterium, Proteus, Providencia, Pseudomonas, Pseudonocardia, Pseudoramibacter, Psychrobacter, Rahnella, Ralstonia, Rhodococcus, Rickettsia, Rochalimaea, Roseomonas, Rothia, Ruminococcus, Salmonella, Selenomonas, Serpulina, Serratia, Shewenella, Shigella, Simkania, Slackia, Sphingobacterium, Sphingomonas, Spirillum, Staphylococcus, Stenotrophomonas, Stomatococcus, Streptobacillus, Streptococcus, Streptomyces, Succinivibrio, Sutterella, Suttonella, Tatumella, Tissierella, Trabulsiella, Treponema, Tropheryma, Tsákamurella, Turicella, Ureaplasma, Vagococcus, Veillonella, Vibrio, Weeksella, Wolinella, Xanthomonas, Xenorhabdus, Yersinia* and *Yokenella*.

For example, the bacterial infection may be caused by a bacterium selected from the group consisting of *Actimomyces europeus, Actimomyces georgiae, Actimomyces gerencseriae, Actimomyces graevenitzii, Actimomyces israelii, Actimomyces meyeri, Actimomyces naeslundii, Actimomyces neuii neuii, Actimomyces neuii anitratus, Actimomyces odontolyticus, Actimomyces radingae, Actimomyces turicensis, Actimomyces viscosus, Arthrobacter creatinolyticus, Arthrobacter cumminsii, Arthrobacter woluwensis, Bacillus anthracis, Bacillus cereus, Bacillus circulans, Bacillus coagulans, Bacillus licheniformis, Bacillus megaterium, Bacillus myroides, Bacillus pumilus, Bacillus sphaericus, Bacillus subtilis, Bacillus thuringiensis, Borrelia afzelii, Borrelia andersonii, Borrelia bissettii, Borrelia burgdorferi, Borrelia garinii, Borrelia japonica, Borrelia lusitaniae, Borrelia tanukii, Borrelia turdi, Borrelia valaisiana Borrelia caucasica, Borrelia crocidurae, Borrelia recurrentis, Borrelia duttoni, Borrelia graingeri, Borrelia hermsii, Borrelia hispanica, Borrelia latyschewii, Borrelia mazzottii, Borrelia parkeri, Borrelia persica, Borrelia recurrentis, Borrelia*

*turicatae, Borrelia venezuelensi, Bordetella bronchiseptica, Bordetella hinzii, Bordetella holmseii, Bordetella parapertussis, Bordetella pertussis, Bordetella trematum, Clostridium absonum, Clostridium argentinense, Clostridium baratii, Clostridium bifermentans, Clostridium beijerinckii, Clostridium butyricum, Clostridium cadaveris, Clostridium carnis, Clostridium celatum, Clostridium clostridioforme, Clostridium cochlearium, Clostridium cocleatum, Clostridium fallax, Clostridium ghonii, Clostridium glycolicum, Clostridium haemolyticum, Clostridium hastiforme, Clostridium histolyticum, Clostridium indolis, Clostridium innocuum, Clostridium irregulare, Clostridium leptum, Clostridium limosum, Clostridium malenominatum, Clostridium novyi, Clostridium oroticum, Clostridium* paraputri, pcum, *Clostridium piliforme, Clostridium putrefasciens, Clostridium ramosum, Clostridium septicum, Clostridium sordelii, Clostridium sphenoides, Clostridium sporogenes, Clostridium subterminale, Clostridium symbiosum, Clostridium tertium, Escherichia coli, Escherichia fergusonii, Escherichia hermanii, Escherichia vulneris, Enterococcus avium, Enterococcus casseliflavus, Enterococcus cecorum, Enterococcus dispar, Enterococcus durans, Enterococcus faecalis, Enterococcus faecium, Enterococcus flavescens, Enterococcus gallinarum, Enterococcus hirae, Enterococcus malodoratus, Enterococcus mundtii, Enterococcus pseudoavium, Enterococcus raffinosus, Enterococcus solitarius, Haemophilus aegyptius, Haemophilus aphrophilus, Haemophilus* par *aphrophilus, Haemophilus parainfluenzae, Haemophilus segnis, Haemophilus ducreyi, Haemophilus influenzae, Klebsiella ornitholytica, Klebsiella oxytoca, Klebsiella planticola, Klebsiella pneumoniae, Klebsiella ozaenae, Klebsiella terrigena, Lysteria ivanovii. Lysteria monocytogenes, Mycobacterium abscessus, Mycobacterium africanum, Mycobacterium alvei, Mycobacterium asiaticum, Mycobacterium aurum, Mycobacterium avium, Mycobacterium bohemicum, Mycobacterium bovis, Mycobacterium branderi, Mycobacterium brumae, Mycobacterium celatum, Mycobacterium chelonae, Mycobacterium chubense, Mycobacterium confluentis, Mycobacterium conspicuum, Mycobacterium cookii, Mycobacterium flavescens, Mycobacterium fortuitum, Mycobacterium gadium, Mycobacterium gastri, Mycobacterium genavense, Mycobacterium gordonae, Mycobacterium goodii, Mycobacterium haemophilum, Mycobacterium hassicum, Mycobacterium intracellulare, Mycobacterium interjectum, Mycobacterium heidelberense, Mycobacterium kansasii, Mycobacterium lentiflavum, Mycobacterium leprae, Mycobacterium malmoense, Mycobacterium marinum, Mycobacterium microgenicum, Mycobacterium microti, Mycobacterium mucogenicum, Mycobacterium neoaurum, Mycobacterium nonchromogenicum, Mycobacterium peregrinum, Mycobacterium phlei, Mycobacterium scrofulaceum, Mycobacterium shimoidei, Mycobacterium simiae, Mycobacterium smegmatis, Mycobacterium szulgai, Mycobacterium terrae, Mycobacterium thermoresistabile, Mycobacterium triplex, Mycobacterium triviale, Mycobacterium tuberculosis, Mycobacterium tusciae, Mycobacterium ulcerans, Mycobacterium vaccae, Mycobacterium wolinskyi, Mycobacterium xenopi, Mycoplasma buccale, Mycoplasma faucium, Mycoplasma fermentans, Mycoplasma genitalium, Mycoplasma hominis, Mycoplasma lipophilum, Mycoplasma orale, Mycoplasma penetrans, Mycoplasma pirum, Mycoplasma pneumoniae, Mycoplasma primatum, Mycoplasma salivarium, Mycoplasma spermatophilum, Pseudomonas aeruginosa, Pseudomonas alcaligenes, Pseudomonas chlororaphis, Pseudomonas fluorescens, Pseudomonas luteola. Pseudomonas mendocina, Pseudomonas monteilii, Pseudomonas oryzihabitans, Pseudomonas pertocinogena, Pseudomonas pseudalcaligenes, Pseudomonas putida, Pseudomonas stutzeri, Rickettsia africae, Rickettsia akari, Rickettsia australis, Rickettsia conorii, Rickettsia felis, Rickettsia honei, Rickettsia japonica, Rickettsia mongolotimonae, Rickettsia prowazeldi, Rickettsia rickettsiae, Rickettsia sibirica, Rickettsia slovaca, Rickettsia typhi, Salmonella choleraesuis choleraesuis, Salmonella choleraesuis arizonae, Salmonella choleraesuis bongori, Salmonella choleraesuis* diarizonae, *Salmonella choleraesuis* houtenae, *Salmonella choleraesuis* indica, *Salmonella choleraesuis* salamae, *Salmonella enteritidis, Salmonella typhi, Salmonella typhimurium, Shigella boydii, Shigella dysentaeriae, Shigella flexnerf, Shigella sonnei, Staphylococcus aureus, Staphylococcus auricularis, Staphylococcus capitis capitis, Staphylococcus c. ureolyticus, Staphylococcus caprae, Staphylococcus aureus, Staphylococcus cohnii cohnii, Staphylococcus c. ureolyticus, Staphylococcus epidermidis, Staphylococcus equorum, Staphylococcus gallinarum, Staphylococcus haemolyticus, Staphylococcus hominis hominis, Staphylococcus* h. novobiosepticius, *Staphylococcus hyicus, Staphylococcus intermedius, Staphylococcus lugdunensis, Staphylococcus pasteuri, Staphylococcus saccharolyticus, Staphylococcus saprophyticus, Staphylococcus* schleiferi schleiferi, *Staphylococcus* s. *coagulans, Staphylococcus sciuri, Staphylococcus simulans, Staphylococcus warneri, Staphylococcus xylosus, Streptococcus agalactiae, Streptococcus canis, Streptococcus dysgalactiae dysgalactiae, Streptococcus dysgalactiae equisimilis, Streptococcus equi* equi, *Streptococcus equi zooepidemicus, Streptococcus iniae, Streptococcus porcinus, Streptococcus pyogenes, Streptococcus anginosus, Streptococcus constellatus constellatus, Streptococcus constellatus* pharyngidis, *Streptococcus intermedius, Streptococcus mitis, Streptococcus oralis, Streptococcus sanguinis, Streptococcus cristatus, Streptococcus gordonii, Streptococcus parasanguinis, Streptococcus salivarius, Streptococcus vestibularis, Streptococcus criceti, Streptococcus mutans, Streptococcus ratti, Streptococcus sobrinus, Streptococcus acidominimus, Streptococcus bovis, Streptococcus equinus, Streptococcus pneumoniae, Streptococcus suis, Vibrio alginolyticus*, V, *carchariae, Vibrio cholerae, C. cincinnatiensis, Vibrio damsela, Vibrio fluvialis, Vibrio furnissii, Vibrio hollisae, Vibrio metschnikovii, Vibrio mimicus, Vibrio* par ahaemolyticus, *Vibrio vulnificus, Yersinia pestis, Yersinia aldovae, Yersinia bercovieri, Yersinia enterocolitica, Yersinia frederiksenii, Yersinia intermedia, Yersinia kristensenii, Yersinia mollaretii, Yersinia pseudotuberculosis* and *Yersinia rohdei.*

Alternatively, the probiotic molecules described herein may find use in treating a virus from a family selected from the group consisting of Astroviridae, Caliciviridae, Picornaviridae, Togaviridae, Flaviviridae, Caronaviridae, Paramyxviridae, Orthomyxoviridae, Bunyaviridae, Arenaviridae, Rhabdoviridae, Filoviridae, Reoviridae, Bornaviridae, Retroviridae, Poxviridae, Herpesviridae, Adenoviridae, Papovaviridae, Parvoviridae, Hepadnaviridae (e.g., a virus selected from the group consisting of a Coxsackie A-24 virus Adeno virus 11, Adeno virus 21, Coxsackie B virus, Borna Diease Virus, Respiratory syncytial virus, Parainfluenza virus, California encephalitis virus, human papilloma virus, varicella zoster virus, Colorado tick fever virus, Herpes Simplex Virus, vaccinia virus, parainfluenza virus 1, parainfluenza virus 2, parainfluenza virus 3, dengue virus, Ebola virus, Parvovirus B19 Coxsackie A-16 virus, HSV-1, hepatitis A virus, hepatitis B virus, hepatitis C virus, hepatitis D virus, hepatitis E virus, human immunodeficiency virus, Coxsackie B1-B5, Influenza viruses A, B or C, LaCross virus, Lassavirus, rubeola virus Coxsackie A or B virus, Echovirus, lymphocytic choriomeningitis virus, HSV-2, mumps virus, Respiratory Synytial Virus, Epstein-Barr Virus, Poliovirus Enterovirus, rabies virus, rubivirus, variola virus, WEE virus, Yellow fever virus and varicella zoster virus).

Alternatively, the probiotic molecules described herein may find use in treating a yeast or fungus. For example, a fungus or yeast that infects a host is selected from the group consisting of *Aspergillus* sp., Dermatophytes, *Blastomyces dermatitidis, Candida* sp., *Histoplasma capsulatum, Sporothrix schenckii, Histoplasma capsulatum* and Dematiaceous Fungi.

As used herein, the term "parasite" or "parasitological infection" shall be taken to mean an organism, whether unicellular or multicellular, other than a virus, bacterium, fungus or yeast that is capable of infecting another organism, for example a human. Examples of such parasites include, for example, a parasite selected from the group consisting of *Ancylostoma ceylanicum, Ancylostoma duodenale, Ascaris lumbricoides, Balantidium coli, Blastocystis hominis, Clonorchis sinensis, Cyclospora cayetanensis, Dientamoeba fragilis, Diphyllobothrium latum, Dipylidium caninum, Encephalitozoon intestinalis, Entamoeba histolytica, Enterobius vermicularis, Fasciola hepatica, Enterobius vermicularis, Fasciola hepatica, Fasciolopsis buski, Giardia intestinalis* (syn. *Giardia lamblia*), *Heterophyes heterophyes, Hymenolepis diminuta, Hymenolepis nana, Isospora belli, Metagonimus yokogawai, Necator americanus, Opisthorchis felineus, Paragonimus westermani, Schistosoma haematobium, Schistosoma intercalatum, Schistosoma japonicum, Schistosoma mansoni, Taenia saginata, Trichuris trichiura, Babesia* diver gens, *Plasmodium falciparum, Plasmodium malariae, Plasmodium ovale, Plasmodium vivax, Leishmania braziliensis* and *Leishmania donovani.*

In aspects, the probiotic molecules could be used generally to reduce biofilm formation or to disrupt already-formed biofilms. The probiotic molecules could also find use in down-regulating virulence genes, typically those associated with T3SS, and in reducing attachment of pathogens to tissue and/or surfaces. The treatment of wounds and treatment and/or prevention of infections in wounds using the probiotic molecules described herein is also contemplated.

In more general aspects, the probiotic molecules could be used as an alternative or adjunct to conventional antibiotic therapies to thereby reduce antibiotic use and mitigate the development of antibiotic resistance.

The probiotic molecules described herein can, in aspects, be administered for example, by parenteral, intravenous, subcutaneous, intradermal, intramuscular, intracranial, intraorbital, ophthalmic, intraventricular, intracapsular, intraspinal, intracisternal, intraperitoneal, intranasal, intrarectal, intravaginal, aerosol or oral administration. Typically, the compositions of the invention are administered orally or directly to the site of infection.

The probiotic molecules described herein may, in aspects, be administered in combination, concurrently or sequentially, with conventional treatments for infection, including antibiotics, for example. The probiotic molecules described herein may be formulated together with such conventional treatments when appropriate.

The probiotic molecules described herein may be used in any suitable amount, but are typically provided in doses comprising from about 1 to about 10000 ng/kg, such as from about 1 to about 1000, about 1 to about 500, about 10 to about 250, or about 50 to about 100 ng/kg, such as about 1, about 10, about 25, about 50, about 75, about 100, about 150, about 200, about 250, about 300, or about 500 ng/kg.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Example 1: Summary of Uropathogenic *E. coli* and Bio-Peptide Identification Purpose:

The purpose of these experiments was to determine if cell-free supernatant from La-5 could down regulate the expression of virulence genes in uropathogenic *E. coli* (UPEC).

Materials and Methods:

The La-5 cell-free supernatant used for these experiments was batch D4. The two UPEC strains were isolated from a dog urinary tract infection. They were provided from the patho-biology lab at the University of Guelph. Strain 1 alias UPEC99 and strain 2 alias UPEC804. The strains were cultured on LB agar. Two different media were tested LB and artificial urine medium.

Primer Sets Tested:

| Gene Alias | Gene Name | FWD or REV | Sequence 5'-3' |
|---|---|---|---|
| FimA | Type-1 Fimbrial protein | FWD | CATCGTTTCCAACGCATCCT (SEQ ID NO: 5) |
| FimA | Type-1 Fimbrial protein | REV | GGTTGCGGCACCAATGGCATAATA (SEQ ID NO: 6) |
| FliC | Flagellin | FWD | ACAGCCTCTCGCTGATCACTCAAA (SEQ ID NO: 7) |
| FliC | Flagellin | REV | GCGCTGTTAATACGCAAGCCAGAA (SEQ ID NO: 8) |
| GapA | Glyceraldehyde 3-phosphate dehydrogenase | FWD | CATCGTTTCCAACGCATCCT (SEQ ID NO: 9) |
| GapA | Glyceraldehyde 3-phosphate dehydrogenase | REV | ACCTTCGATGATGCCGAAGTT (SEQ ID NO: 10) |
| PapA_2 | Major Pilus P fimbrial | FWD | GTGCCTGCAGAAAATGCAGAT (SEQ ID NO: 11) |
| PapA_2 | Major Pilus P fimbrial | REV | CCCGTTTTCCACTCGAATCA (SEQ ID NO: 12) |
| HylA | Hemolysin A | FWD | ACCTTGTCAGGACGGCAGAT (SEQ ID NO: 13) |
| HylA | Hemolysin A | REV | CCGTGCCATTCTTTTCATCA (SEQ ID NO: 14) |
| TufA | Elongation factor Tu | FWD | ACTTCCCGGGCGACGACACTC (SEQ ID NO: 15) |

-continued

| Gene Alias | Gene Name | FWD or REV | Sequence 5'-3' |
|---|---|---|---|
| TufA | Elongation factor Tu | REV | CGCCCGGCATTACCATCTCT AC (SEQ ID NO: 16) |

Assays were performed similarly as the *Salmonella* assays, as described in Sharma 2014. The UPEC were grown for 4 hours in the presence of cell-free supernatant. The cells were harvested and the RNA was extracted. The RNA was treated with DNAse I to remove genomic DNA. The RNA was used as a template to make cDNA. The cDNA was assayed by qPCR and the gene expression was normalized to a reference gene and compared to a without cell-free media control.

Results:

TABLE 1.1

Comparison of Gene expression with LB and artificial urine medium.

| Gene Target | Strain | Media | Reference Gene | Down Regulation |
|---|---|---|---|---|
| FliC | Strain 1 (E99) | LB | GapA | 0.024 |
| FliC | Strain 1 (E99) | Artificial Urine Media | GapA | 0.014 |
| FliC | Strain 2 (E804) | LB | GapA | 0.56 |
| FliC | Strain 2 (E804) | Artificial Urine Media | GapA | 0.045 |
| HylA | Strain 1 (E99) | LB | GapA | 16.47 |
| HylA | Strain 1 (E99) | Artificial Urine Media | GapA | 1.35 |
| HylA | Strain 2 (E804) | LB | GapA | Not Expressed |
| HylA | Strain 2 (E804) | Artificial Urine Media | GapA | Not Expressed |
| FimA | Strain 1 (E99) | LB | GapA | Not Expressed |
| FimA | Strain 1 (E99) | Artificial Urine Media | GapA | Not Expressed |
| FimA | Strain 2 (E804) | LB | GapA | Not Expressed |
| FimA | Strain 2 (E804) | Artificial Urine Media | GapA | Not Expressed |

The data in Table 1.1 suggested that the cell-free supernatant is effective at down regulating HylA, but not FliC. There is also more down regulation in LB media of HylA compared to the artificial urine media. The expression of these genes was further investigated with only LB media since it has a higher down regulation of genes. This experiment was tested again to confirm that the response was strain specific.

TABLE 1.2

Comparison strain specific gene regulation.

| Gene Target | Strain | Media | Reference Gene | Down Regulation |
|---|---|---|---|---|
| FliC | Strain 1 (E99) | LB | GapA | 1.90 |
| FliC | Strain 2 (E804) | LB | GapA | 0.705 |
| HylA | Stain 1 (E99) | LB | GapA | 12.72 |
| HylA | Strain 2 (E804) | LB | GapA | Not Expressed |

The data in Table 1.2 suggests that the cell-free supernatant can down regulate HylA but only is strain 1, since HylA does not seem to be expressed in strain 2. The cell-free supernatant does not appear to effect the down regulation of FliC.

TABLE 1.3

Dose response curve of batch D4 and UPEC Strain 1 (E99)

| Gene Target | Dose | Reference Gene | Down Regulation |
|---|---|---|---|
| HylA | 4× | GapA | 40.46 |
| HylA | 2× | GapA | 19.86 |
| HylA | 1× | GapA | 24.69 |
| HylA | 0.5× | GapA | 4.90 |
| HylA | 0.25× | GapA | 2.79 |

The 1×dose is equivalent to 10 mL of cell-free supernatant (1×). The down regulation of HylA correlates with the amount of material assayed. This suggests that the cell-free supernatant has a specific interaction with the regulation of HylA and potential down-stream mechanisms.

TABLE 1.4

Summary table of HylA gene expression in strain 1 (E99) with stability batch (S1).

| Target Gene | Treatment | Reference Gene | Fold Down Regulation HylA |
|---|---|---|---|
| HylA | E99 0.25× | GapA | 0.98 |
| HylA | E99 0.5× | GapA | 3.16 |
| HylA | E99 1× | GapA | 6.96 |
| HylA | E99 2× | GapA | 10.85 |

The 1×dose is equivalent to 10 mL of cell-free supernatant (1×). A second batch of material was tested to determine in the dry cell-free supernatant for an additional independent production batch could also down regulation of HylA expression. There was a dose response with the amount of dry cell-free supernatant tested and the down regulation of HylA.

Example 2: Identification of Bioactive Molecules from Cell-Free Supernatant

Purpose:

The purpose of these experiments was to identify the bioactive peptides from the cell-free supernatant.

Materials and Methods:

The cell-free supernatant was separated using Sephadex G75 resin. The samples were separated and collected into fractions: Fraction 1 (>163000 Da), Fraction 2 (163000-14500 Da), Fraction 3(14500-1300 Da), Fraction 4 (1300-110 Da), Fraction 5 (110-10 Da). The samples were collected and assayed by qPCR using *Salmonella* enteric *typhimurium* DT104 strain. The down-regulation of HilA was compared to the reference gene 16S.

```
Primers:
HilA FWD
                                  (SEQ ID NO: 17)
5'-3'-TGTCGGAAGATAAAGAGCAT

HilA REV
                                  (SEQ ID NO: 18)
5'-3'-AAGGAAGTATCGCCAATGTA

16S FWD
                                  (SEQ ID NO: 19)
5'-3'-CAAGTCATCATGGCCCTTAC

16S REV
                                  (SEQ ID NO: 20)
5'-3'-CGGACTACGACGCACTTTAT
```

The active fraction from G75 size exclusion chromatography was further separated using reverse phase chromatography. The fractions from the reverse phase: Fraction 1 (0-2 min), Fraction 2 (2-4 min), Fraction 3 (4-16 min), Fraction 4 (16-32 min), Fraction 5 (32-40 min), Fraction 6 (40-58 min). The fractions were dried and neutralized to remove acetonitrile and trifluoroacetic acid from the solvent. The dried fractions were assayed using the same qPCR assay conditions as above. The fractions were analyzed by de novo sequencing at the University of Guelph Advance Analytical center. The peptides from the active fractions of 6 batches were compared and common peptides from batches were deduced.

TABLE 2.1 qPCR down-regulation of Size exclusion fractions

| Treatment | Target Gene | Reference Gene | Down-Fold Regulation |
|---|---|---|---|
| Input | HilA | 16S | 14.36 |
| Fraction 1 | HilA | 16S | 1.38 |
| Fraction 2 | HilA | 16S | 2.98 |
| Fraction 3 | HilA | 16S | 10.97 |
| Fraction 4 | HilA | 16S | 1.84 |
| Fraction 5 | HilA | 16S | 3.30 |

The size-exclusion fraction 3 was further characterized since it had similar activity as the input suggesting that the activity of this fraction is the major component of the bio-active molecules.

TABLE 2.2 qPCR down-regulation of reverse phase (RP) fraction purified from size exclusion Fraction 3

| Treatment | Target Gene | Reference Gene | Down-Fold Regulation |
|---|---|---|---|
| RP Fraction 1 | HilA | 16S | 1.15 |
| RP Fraction 2 | HilA | 16S | 0.68 |
| RP Fraction 3 | HilA | 16S | 3.78 |
| RP Fraction 4 | HilA | 16S | 0.56 |
| RP Fraction 5 | HilA | 16S | 169 |
| RP Fraction 6 | HilA | 16S | 0.0096 |

The RP fractions 3 and 5 were selected for de novo sequencing the results are from fraction 5 as it had the most activity noting that MALPPK has also found in RP fraction 3 but the other peptides were only found in fraction 5.

TABLE 2.3

De novo sequencing RP fraction 5 biopeptides analyzed from 6 production batches

| | Batch Number | | | | | |
|---|---|---|---|---|---|---|
| Peptide Sequence | D4 | D8 | D10 | D14 | D15 | P64 |
| MALPPK (SEQ ID NO: 21) | Present | Present | Present | Present | Present | Present |
| CVLPPK (SEQ ID NO: 22) | Present | Present | Present | Present | Present | Present |
| HLLPLP (SEQ ID NO: 23) | Present | Present | Present | Present | ND | ND |
| LKPTPEGD (SEQ ID NO: 24) | ND | Present | Present | Present | Present | ND |

De novo sequencing was used to identify amino acid sequences that are responsible for the down-regulation of virulence genes such as HilA in the *Salmonella enterica typhimurium* DT104. Six independent production batches were analyzed. The cell-free supernatant was separated using size-exclusion chromatography (Sephadex G75). The samples were isolated into 5 fractions based on their molecular mass. The third fraction with a predicted molecular weight range of 14.5-1.3 kDa was further analyzed by reverse phase chromatography and fraction RP 5 was analyzed by de novo sequencing. A comparison of all of the bio-peptides analyzed identified two peptides that were common between all six batches and two additional peptides that were common to at least 4 batches. Since de novo sequencing is only a qualitative analysis all four of these peptides were synthesized to identify which peptides are responsible for the down-regulation of HilA in *Salmonella* enteric *typhimurium* DT104.

TABLE 2.4

Semi-quantification of biopeptides from size-exclusion fraction 3 of stability batch 1 (S1)

| Peptide Sequence | Peptide Concentration (ng/mL) |
|---|---|
| MALPPK (SEQ ID NO: 21) | 2500 |
| CVLPPK (SEQ ID NO: 22) | Below detection limit |
| HLLPLP (SEQ ID NO: 23) | 2.5-5 |
| LKPTPEGD (SEQ ID NO: 24) | 25-50 |
| YPVEPF (SEQ ID NO: 1) | 10-25 |
| YPPGGP (SEQ ID NO: 2) | 100 |

The selected bio-peptides from de novo sequencing and two additional peptides that were identified in International Patent Application Publication No. WO 2009/155711 were analyzed mass spectroscopy using multiple reaction monitoring (MRM) mode to semi-quantify the amount of bio-peptide present in the stability batch S1. The peak height of each peptide was compared to the peak height of a dilution series of a known amount of each bio-peptide. This semiquantitative method identified that MALPPK was the most abundant peptide present of the 6 peptides analyzed.

TABLE 2.5 qPCR analysis of the change in expression of HylA and HilA in the presence of individual synthetic biopeptides

| Peptide Sequence | Target Gene | Reference Gene | Fold down-regulation |
|---|---|---|---|
| MALPPK (SEQ ID NO: 21) | HylA | GapA | 9.06 |
| CVLPPK (SEQ ID NO: 22) | HylA | GapA | 3.20 |
| HLLPLP (SEQ ID NO: 23) | HylA | GapA | 2.64 |
| LKPTPEGD (SEQ ID NO: 24) | HylA | GapA | 4.69 |
| YPVEPF (SEQ ID NO: 1) | HylA | GapA | 1.03 |
| YPPGGP (SEQ ID NO: 2) | HylA | GapA | 3.56 |
| MALPPK (SEQ ID NO: 21) | HilA | 16S | 19.56 |
| CVLPPK (SEQ ID NO: 22) | HilA | 16S | 3.75 |
| HLLPLP (SEQ ID NO: 23) | HilA | 16S | 2.93 |
| LKPTPEGD (SEQ ID NO: 24) | HilA | 16S | 11.08 |
| YPVEPF (SEQ ID NO: 1) | HilA | 16S | 0.68 |
| YPPGGP (SEQ ID NO: 2) | HilA | 16S | 2.93 |

The synthetic bio-peptides were analyzed at 50 μg per assay. The qPCR analysis suggests that all of the peptides affect the down-regulation of HylA except YPVEPF (SEQ ID NO: 1). The peptide MALPPK (SEQ ID NO: 21) appears to have the highest effect on the down-regulation of HylA followed by LKPTPEGD (SEQ ID NO: 24), YPPGGP (SEQ ID NO: 2), CVLPPK (SEQ ID NO: 22), and HLLPLP (SEQ ID NO: 23).

SUMMARY

The data presented in tables 2.1-2.5 demonstrate that peptides found in the cell-free supernatant of La-5 fermentation media can down-regulate the expression of HilA in *Salmonella enterica typhimurium* DT104 and Hemolysin A (HylA). HylA is a pore-forming toxin produced by UPEC and is one of the virulence factors involved in infection. The interaction appears to be specific since the expression of flagellin (FliC) is not down-regulated in the presence of the cell-free supernatant. Two independent production batches demonstrated a specific down-regulation of HylA in a dose dependent manner. Four peptides were identified from de novo sequencing of size exclusion fraction 3. These four peptides and two additional peptides from a previous patent were synthesized and their effect on HylA gene expression was quantified by qPCR. All of the bio-peptides except YPVEPF were active and MALPPK was the most active peptide of the 6 peptides analyzed.

Example 3: Uropathogenic *E. coli* Cell Toxicity Assay

Purpose:

The purpose of this experiment was to determine if there was a reduction in toxin production in uropathogenic *E. coli* in the present *Lactobacillus acidophilus* cell-free media using a physiological cell toxicity assay.

Materials and Methods:

The dried cell free supernatant was dissolved into LB broth (14 mg/mL) and was adjusted using to pH 7.2 using 0.1 N NaOH. The solution was diluted with LB broth to the final concentration. The broth (5 mL) was inoculated with 50 μL of an 18 hr UPEC099 strain culture. The sample was grown for 4 hours at 37° C. with 200 rpm agitation. A 1 mL aliquot of the culture was centrifuged at 10,000×g to remove the *E. coli* cells. The supernatant (100 μL) was added to 1 mL of HT29 mammalian cells (1E6 cells/mL) and incubated for 1 hr at 37° C. supplemented with 5% $CO_2$. After the incubation the mixture was transferred to an 1.5 mL tube and centrifuged at 250×g to remove the mammalian cells. The supernatant (50 μL) was used to test for cell toxicity using the Pierce Lactate Dehydrogenase LDH cytotoxicity assay (Thermo Fisher Scientific). The solutions for the assay were prepared according to the manufacturer's instructions. The 50 μL of supernatant was incubated with 50 μL of assay reaction mixture in a 96 well plate. The assay was covered the foil to protect it from light and incubated at room temperature for 30 minutes. The reaction stop (50 μL) mixture was added and the 96-well plate was read at 490 nm and 680 nm. The absorbance values were used to calculate the cytotoxicity, the data is expressed as percent inhibition.

Figure 2:
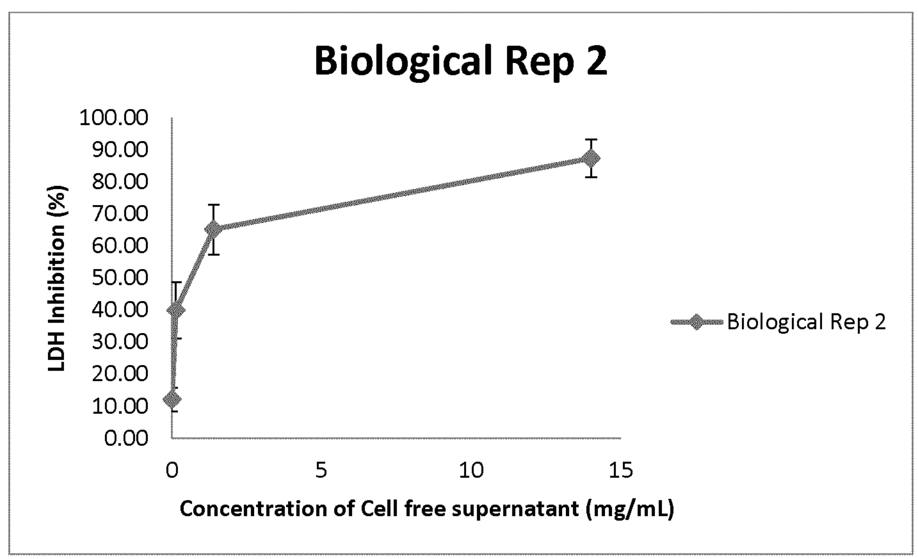
FIG. 2 shows a lactate dehydrogenase cell toxicity assay. Dose response curve of cell toxicity inhibition with cell free supernatant. Error bars represent standard deviation.

Results/Discussion:

The data presented in FIGS. 1 and 2 represent the inhibition of UPEC toxin production with the cell free supernatant. These data provide physiological support that the cell free supernatant is able to reduce the effect of toxin on the HT29 mammalian cells in a dose dependent manner. Lactate dehydrogenase is a physiological marker for cell lysis and inhibition of lactate dehydrogenase in an end-point assay suggests that fewer mammalian cells have been lysed inferring that the cell free supernatant can reduce the amount of toxin produced by UPEC099.

Example 4: Overcoming Drug Resistance

Purpose:

To determine if cell-free supernatant from probiotic bacteria, such as *Lactobacillus acidophilus* La-5, could increase the sensitivity of drug resistant bacteria to antibiotics, specifically methicillin resistant Staphylococci to cefoxitin.

Materials and Methods:

The La-5 cell-free supernatant used for these experiments was obtained from batches N9-N10 and N13. Three methicillin resistant Staphylococci (MRS) strains were used in these experiments: 1) *Staphylococcus* pseudintermedius (strain alias C260 22-2011 dtqa), a clinical isolate from a dog skin infection; 2) *Staphylococcus aureus* (strain alias LA-414M SPA t034), a livestock-associated strain isolated from beef purchased from a grocery store in Charlottetown, PEI, Canada; and 3) *Staphylococcus aureus* (strain alias 81M SPA t008), isolated from poultry meat purchased from a grocery store in Charlottetown, PEI, Canada. All three MRS strains were provided by the Atlantic Veterinary College (AVC) at the University of Prince Edward Island. The methicillin-resistance of these strains was confirmed by AVC staff using an oxacillin disk diffusion method. The strains were originally cultured on sheep blood agar slants, and then transferred to lysogeny broth agar plates. Cefoxitin resuspended in methanol was used for antibiotic resistance testing, and growth was tested in two different media types, standard Lysogeny Broth and standard BBL™ Cation-Adjusted Mueller-Hinton Medium (Becton, Dickinson and Company). The minimum inhibitory concentrations (MICs) of the cefoxitin was determined for each strain in each respective medium in the presence and absence of the cell-free supernatant. Assays were performed according to the Clinical and Laboratory Standards Institute (CLSI) guidelines for MIC testing of Staphylococcal species [CLSI, 2015] as well as the European Committee for Antimicrobial Susceptibility Testing (EUCAST) of the European Society of Clinical Microbiology and Infectious Diseases [EUCAST, 2003].

The protocol for MIC testing was as follows. The cell-free supernatants were resuspended in the respective media and filter sterilized through a 0.22 μM pore size filter. The required concentration of dried cell free supernatant was weighed and added at concentrations ranging from 0-60 mg/mL. Cefoxitin was added to obtain final concentrations ranging from 0-250 μg/mL. Cultures of each respective strain were grown overnight in either lysogeny broth or Mueller Hinton for 16-20 hours at 37° C. and 200 rpm shaking in aerobic conditions to achieve optical densities at 600 nm (OD600) of 1.2-1.6. Overnight cultures were diluted 1,000-fold and inoculated into the respective samples; this dilution of overnight culture resulted in an inoculum containing about $5\times10^6$ CFU/mL. The cultures (150 μL) were grown in a 96-well clear flat-bottom microtiter plate. The microtiter plate was then covered in parafilm and incubated at 35° C.±2° C. for 24 hours. Following incubation, microplates were read at 600 nm using a microplate reader. The MIC value was the concentration of the antibiotic which resulted in an OD600 reading of <0.1. The data is the average from two technical replicates from two biological replicates.

β-Lactams such as methicillin and cefoxitin inhibit bacterial cell wall biosynthesis. Bacteria have evolved mechanisms to evade these inhibitors leading to antibiotic resistance. MecA is a gene that can bind to β-lactams thereby reducing their activity. Staphylococci that have acquired the MecA gene are methicillin resistant. The expression of MecA is regulated by quorum sensing therefore we investigated if the cell-free supernatant could increase the susceptibility of methicillin resistant Staphylococci by inhibiting quorum sensing.

The data show that cell free supernatant can increase the susceptibility of methicillin resistant Staphylococci species to cefoxitin antibiotic; this in turn reduces the concentration of cefoxitin required to halt or prevent methicillin resistant Staphylococci species from proliferating. For the tested concentrations of cell free supernatant (5 mg/mL, 30 mg/mL, and 60 mg/mL) the data indicate a dose response: as the cell free supernatant concentration increases, there is a greater reduction in the cefoxitin MIC compared to the 0 mg/mL control. The combination of cefoxitin and cell-free supernatant can increase the susceptibility methicillin resistant Staphylococci by 2.5-6.25 fold compared to cefoxitin only (Table 3).

TABLE 3

Range of cefoxitin MIC values for methicillin resistant Staphylococci

| Concentration of dried cell-free per assay (mg/mL) | Range of Cefoxitin concentration (μg/mL) to inhibition growth to O.D. < 0.1 | | | | |
|---|---|---|---|---|---|
| | MSRP C260 Lysogeny Broth | MRSA LA 414M Lysogeny Broth | MRSA LA 414M Mueller-Hinton Broth | MRSA 81M Lysogeny Broth | MRSA 81M Mueller-Hinton Broth |
| 0 | 125-175 | 30-40 | 50-60 | 75-125 | 75-100 |
| 5 | 50-75 | 15-20 | 40-50 | 40-50 | 40-50 |
| 30 | 20-30 | 15-20 | 20-30 | 30-40 | 30-40 |
| 60 | 20-30 | 10-15 | 20-30 | 30-40 | 20-30 |

For the size exclusion chromatography the sample was separated using a Sephadex G75 resin. The samples were separated and collected into fractions: Fraction 1 (>163000 Da), Fraction 2 (163000-14500 Da), Fraction 3(14500-1300 Da), Fraction 4 (1300-110 Da), Fraction 5 (110-10 Da). The methicillin resistant *Staphylococcus aureus* 81M was most susceptible to cefoxitin when co-incubated with size exclusion fraction 3. This data indicates that the active component is in size exclusion fraction 3 (Table 4), strongly suggesting that the bioactive molecules responsible for this effect are the same as those described and characterized herein.

TABLE 4

Range of cefoxitin MIC values for methicillin resistant *Staphylococcus aureus* 81M with size exclusion fractions of cell-free supernatant

| Controls | Range of Cefoxitin concentration (μg/mL) to inhibition growth to O.D. < 0.1 |
|---|---|
| Untreated (0 mg/mL) | 60-75 |
| Cell-free supernatant (30 mg/mL) | 20-30 |
| Size Exclusion Fraction Number | |
| Fraction 1 | 60-75 |
| Fraction 2 | 75-100 |
| Fraction 3 | 30-40 |
| Fraction 4 | 60-75 |
| Fraction 5 | 40-50 |

The above disclosure generally describes the present invention. Although specific terms have been employed herein, such terms are intended in a descriptive sense and not for purposes of limitation.

All publications, patents and patent applications cited above are herein incorporated by reference in their entirety to the same extent as if each individual publication, patent or patent application was specifically and individually indicated to be incorporated by reference in its entirety.

Although preferred embodiments of the invention have been described herein in detail, it will be understood by those skilled in the art that variations may be made thereto without departing from the spirit of the invention or the scope of the appended claims.

The invention claimed is:

1. An object for preventing and/or treating a non-enteric infection in a subject and/or reducing the virulence of a non-enteric infection in a subject, the object comprising a peptide produced by probiotic bacteria, the object being a stent, catheter, or wound dressing comprising the peptide, wherein the peptide is capable of preventing and/or treating the non-enteric infection in the subject and/or the peptide is capable of reducing the virulence of the non-enteric infection in the subject, and wherein the object is capable of releasing the peptide over a period of time.

2. The object of claim 1, wherein the probiotic bacteria is selected from *Lactobacillus, Lactococcus, Streptococcus, Bifidobacterium, Pediococcus, Enterococcus*, and combinations thereof.

3. The object of claim 1, wherein the peptide is concentrated from a cell-free supernatant of a culture medium, or a fraction thereof, in which the probiotic bacteria are grown.

4. The object of claim 1, wherein the probiotic bacteria are grown in a liquid culture medium and the peptide is provided as a dried culture fraction from the liquid culture medium.

5. The object of claim 4, wherein the dried culture fraction is a dried cell-free supernatant from the liquid culture medium.

6. The object of claim 1, wherein the peptide comprises a sequence selected from the group consisting of YPVEPF (SEQ ID NO: 1), YPPGGP (SEQ ID NO: 2), YPPG (SEQ ID NO: 3), NQPY (SEQ ID NO: 4), and combinations thereof.

7. The object of claim 1, wherein the peptide is not a bacteriocin.

* * * * *

UNITED STATES PATENT AND TRADEMARK OFFICE
CERTIFICATE OF CORRECTION

PATENT NO. : 11,912,788 B2
APPLICATION NO. : 16/494429
DATED : February 27, 2024
INVENTOR(S) : Cella et al.

It is certified that error appears in the above-identified patent and that said Letters Patent is hereby corrected as shown below:

In the Specification

Column 17, Line 15: Please correct “paraputri, pcum,” to read --paraputriβcum,--

Column 18, Line 15: Please correct “flexnerf,” to read --flexneri,--

Signed and Sealed this
Fourteenth Day of May, 2024

Katherine Kelly Vidal

Katherine Kelly Vidal
*Director of the United States Patent and Trademark Office*

SEQUENCE LISTING

<160> NUMBER OF SEQ ID NOS: 24

<210> SEQ ID NO 1
<211> LENGTH: 6
<212> TYPE: PRT
<213> ORGANISM: Artificial Sequence
<220> FEATURE:
<223> OTHER INFORMATION: Peptide

<400> SEQUENCE: 1

Tyr Pro Val Glu Pro Phe
1               5

<210> SEQ ID NO 2
<211> LENGTH: 6
<212> TYPE: PRT
<213> ORGANISM: Artificial Sequence
<220> FEATURE:
<223> OTHER INFORMATION: Peptide

<400> SEQUENCE: 2

Tyr Pro Pro Gly Gly Pro
1               5

<210> SEQ ID NO 3
<211> LENGTH: 4
<212> TYPE: PRT
<213> ORGANISM: Artificial Sequence
<220> FEATURE:
<223> OTHER INFORMATION: Peptide

<400> SEQUENCE: 3

Tyr Pro Pro Gly
1

<210> SEQ ID NO 4
<211> LENGTH: 4
<212> TYPE: PRT
<213> ORGANISM: Artificial Sequence
<220> FEATURE:
<223> OTHER INFORMATION: Peptide

<400> SEQUENCE: 4

Asn Gln Pro Tyr
1

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
catcgtttcc aacgcatcct                                                    20

<210> SEQ ID NO 6
<211> LENGTH: 24
<212> TYPE: DNA
<213> ORGANISM: Artificial Sequence
<220> FEATURE:
<223> OTHER INFORMATION: Primer

<400> SEQUENCE: 6
ggttgcggca ccaatggcat aata                                               24

<210> SEQ ID NO 7
<211> LENGTH: 24
<212> TYPE: DNA
<213> ORGANISM: Artificial Sequence
<220> FEATURE:
<223> OTHER INFORMATION: Primer

<400> SEQUENCE: 7
acagcctctc gctgatcact caaa 24

<210> SEQ ID NO 8
<211> LENGTH: 24
<212> TYPE: DNA
<213> ORGANISM: Artificial Sequence
<220> FEATURE:
<223> OTHER INFORMATION: Primer

<400> SEQUENCE: 8
gcgctgttaa tacgcaagcc agaa 24

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
catcgtttcc aacgcatcct 20

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
accttcgatg atgccgaagt t 21

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
gtgcctgcag aaaatgcaga t 21

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
cccgttttcc actcgaatca 20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
accttgtcag gacggcagat 20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
ccgtgccatt cttttcatca 20

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
acttcccggg cgacgacact c 21

<210> SEQ ID NO 16
<211> LENGTH: 22
<212> TYPE: DNA
<213> ORGANISM: Artificial Sequence
<220> FEATURE:
<223> OTHER INFORMATION: Primer

<400> SEQUENCE: 16
cgcccggcat taccatctct ac 22

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
tgtcggaaga taaagagcat 20

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
aaggaagtat cgccaatgta 20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
caagtcatca tggcccttac 20

-continued

```
<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20

cggactacga cgcactttat                                             20


<210> SEQ ID NO 21
<211> LENGTH: 6
<212> TYPE: PRT
<213> ORGANISM: Artificial Sequence
<220> FEATURE:
<223> OTHER INFORMATION: Peptide

<400> SEQUENCE: 21

Met Ala Leu Pro Pro Lys
1               5


<210> SEQ ID NO 22
<211> LENGTH: 6
<212> TYPE: PRT
<213> ORGANISM: Artificial Sequence
<220> FEATURE:
<223> OTHER INFORMATION: Peptide

<400> SEQUENCE: 22

Cys Val Leu Pro Pro Lys
1               5


<210> SEQ ID NO 23
<211> LENGTH: 6
<212> TYPE: PRT
<213> ORGANISM: Artificial Sequence
<220> FEATURE:
<223> OTHER INFORMATION: Peptide

<400> SEQUENCE: 23

His Leu Leu Pro Leu Pro
1               5


<210> SEQ ID NO 24
<211> LENGTH: 8
<212> TYPE: PRT
<213> ORGANISM: Artificial Sequence
<220> FEATURE:
<223> OTHER INFORMATION: Peptide

<400> SEQUENCE: 24

Leu Lys Pro Thr Pro Glu Gly Asp
1               5
```